(12) United States Patent
Yan et al.

(10) Patent No.: US 12,216,073 B2
(45) Date of Patent: Feb. 4, 2025

(54) HYDROGEN-SENSITIVE MATERIAL RESISTANT TO HUMIDITY INTERFERENCE, SEMICONDUCTOR RESISTIVE HYDROGEN SENSOR, AND INTELLIGENT HYDROGEN SENSING SYSTEM, AND PREPARATION METHOD AND USE THEREOF

(71) Applicant: Jiangsu University, Jiangsu (CN)

(72) Inventors: Jia Yan, Jiangsu (CN); Zhilong Song, Jiangsu (CN); Hui Xu, Jiangsu (CN); Huaming Li, Jiangsu (CN)

(73) Assignee: JIANGSU UNIVERSITY, Jiangsu (CN)

(*) Notice: Subject to any disclaimer, the term of this patent is extended or adjusted under 35 U.S.C. 154(b) by 0 days.

(21) Appl. No.: 18/882,115

(22) Filed: Sep. 11, 2024

(65) Prior Publication Data

US 2025/0003910 A1 Jan. 2, 2025

Related U.S. Application Data

(63) Continuation of application No. PCT/CN2023/084306, filed on Mar. 28, 2023.

(30) Foreign Application Priority Data

Mar. 6, 2023 (CN) .......................... 202310204483.6

(51) Int. Cl.
*G01N 27/12* (2006.01)
*G01N 33/00* (2006.01)

(52) U.S. Cl.
CPC ......... *G01N 27/123* (2013.01); *G01N 33/005* (2013.01)

(58) Field of Classification Search
CPC .......................... G01N 27/123; G01N 33/005
See application file for complete search history.

(56) References Cited

U.S. PATENT DOCUMENTS

| 11,493,493 | B2* | 11/2022 | Drmosh | G01N 27/4075 |
| 2013/0202489 | A1* | 8/2013 | Ong | G01N 33/005 977/902 |
| 2019/0376940 | A1* | 12/2019 | Debnath | G01N 33/004 |

* cited by examiner

*Primary Examiner* — Jermele M Hollington
*Assistant Examiner* — Zannatul Ferdous
(74) *Attorney, Agent, or Firm* — Tutunjian & Bitetto, P.C.

(57) ABSTRACT

Provided are a hydrogen-sensitive material resistant to humidity interference, a semiconductor resistive hydrogen sensor, and an intelligent hydrogen sensing system, and a preparation method and use thereof, which relate to the technical field of gas sensors. The hydrogen-sensitive material resistant to humidity interference includes a three-dimensional (3D) porous non-conductive metal oxide substrate, a nano-scale $WO_{3-x}$ film deposited on an outer surface and an inner pore surface of the 3D porous non-conductive metal oxide substrate, and Pd nanoclusters diffusely distributed on a surface of the nano-scale $WO_{3-x}$ film, wherein the nano-scale $WO_{3-x}$ film is formed from oxygen vacancy-containing tungsten oxide.

12 Claims, 12 Drawing Sheets

HYDROGEN-SENSITIVE MATERIAL RESISTANT TO HUMIDITY INTERFERENCE, SEMICONDUCTOR RESISTIVE HYDROGEN SENSOR, AND INTELLIGENT HYDROGEN SENSING SYSTEM, AND PREPARATION METHOD AND USE THEREOF

CROSS REFERENCE TO RELATED APPLICATION

The present application is a continuation application of International Patent Application No. PCT/CN2023/084306, filed on Mar. 28, 2023, which claims priority to Chinese Patent Application No. 202310204483.6, entitled "Hydrogen-sensitive material resistant to humidity interference, semiconductor resistive hydrogen sensor, and intelligent hydrogen sensing system, and preparation method and use thereof", and filed with the China National Intellectual Property Administration on Mar. 6, 2023. The disclosure of the two applications is incorporated by references herein in their entireties as part of the present application.

TECHNICAL FIELD

The present disclosure relates to the technical field of gas sensors, and in particular to a hydrogen-sensitive material resistant to humidity interference, a semiconductor resistive hydrogen sensor, and an intelligent hydrogen sensing system, and a preparation method and use thereof.

BACKGROUND

Gas sensors have an ability to perceive surroundings, including detection of chemical analytes, exhaled gases, and flammable and explosive gases, gas leakage detection, environmental monitoring, disease diagnosis, or the like. As a result, gas sensors play a vital role in daily routines. With the development of Internet technology, intelligent, low-power, and high-integration-level gas sensors are becoming more and more popular. High performance (high sensitivity, high selectivity, and portability) of gas sensors has always been pursued.

Metal oxide semiconductor (MOS)-based sensors, especially $SnO_2$-based resistive gas sensors, have been proven to be a suitable material and have been widely used on the market due to characteristics such as easiness of manufacture, simple operations, and low production costs. Individual gas sensor could be randomly distributed at any corner of a room to form a gas sensor array, which could continuously monitor a quality of indoor air for a long time and identify toxic and harmful gases, such as leaked flammable and explosive gases (such as $H_2$ and $NO_2$) and chemical analytes (such as formaldehyde and toluene) at low concentrations (part per billion (ppb)) in freshly-decorated rooms. However, most MOS-based sensors always face the problem that there are false alarms due to poor selectivity. In particular, a humidity in an environment is always changing, and the changing humidity would interact with a surface of a semiconductor to cause a change of an electrical signal (initial resistance and sensitivity). Therefore, the interference of humidity would adversely affect the selective identification of a target gas.

Currently, there is no hydrogen sensor resistant to humidity interference on the market. With the development of hydrogen energy, the selective detection of hydrogen has become an urgent problem to be solved.

SUMMARY

In view of this, an object of the present disclosure is to provide a hydrogen-sensitive material resistant to humidity interference, a semiconductor resistive hydrogen sensor, and an intelligent hydrogen sensing system, and a preparation method and use thereof. The hydrogen-sensitive material provided by the present disclosure has an ability to resist humidity interference, and exhibits excellent selectivity for hydrogen.

To allow the object of the present disclosure, the present disclosure provides the following technical solutions:

The present disclosure provides a hydrogen-sensitive material resistant to humidity interference, including a three-dimensional (3D) porous non-conductive metal oxide substrate, a nano-scale $WO_{3-x}$ film deposited on an outer surface and an inner pore surface of the 3D porous non-conductive metal oxide substrate, and Pd nanoclusters diffusely distributed on a surface of the nano-scale $WO_{3-x}$ film, wherein the nano-scale $WO_{3-x}$ film is formed from oxygen vacancy-containing tungsten oxide.

In some embodiments, the 3D porous non-conductive metal oxide substrate has a thickness of 10 μm to 1 mm and a pore size of 50 nm to 400 nm.

In some embodiments, the nano-scale $WO_{3-x}$ film has a thickness of 5 nm to 50 nm; and the Pd nanoclusters have a particle size of 0.5 nm to 5 nm, and a mass content of the Pd nanoclusters in the hydrogen-sensitive material ranges from 0.1% to 10%.

The present disclosure provides a method for preparing the hydrogen-sensitive material resistant to humidity interference as described in the above technical solutions, including the following steps:

conducting a first atomic layer deposition (ALD) on the 3D porous non-conductive metal oxide substrate by using bis(tert-butylimino)bis(dimethylamino)tungsten (VI) as a tungsten source and ozone as a precursor source, to obtain a nano-scale $WO_{3-x}$ film-deposited 3D porous substrate, wherein the first ALD is conducted at a temperature of 200° C. to 400° C., and an introduction time ratio of the tungsten source to the ozone is in a range of 1:1 to 1:2.5; and conducting a second ALD on the nano-scale $WO_{3-x}$ film-deposited 3D porous substrate by using bis(hexafluoroacetylacetonato) palladium as a Pd source and vaporized anhydrous hydrazine as a precursor source, to obtain the hydrogen-sensitive material resistant to humidity interference, wherein the second ALD is conducted at a temperature of 180° C. to 220° C.

In some embodiments, the first ALD is conducted 50 to 500 times, and a $WO_{3-x}$ film formed after a single time of the first ALD has a thickness of 0.05 nm to 0.2 nm.

In some embodiments, the second ALD is conducted 1 to 100 times.

The present disclosure provides a semiconductor resistive hydrogen sensor, including the hydrogen-sensitive material resistant to humidity interference as described in the above technical solutions or the hydrogen-sensitive material resistant to humidity interference prepared by the method as described in the above technical solutions, a heating electrode fixed on a surface of one side of the hydrogen-sensitive material, and a sensing electrode fixed on a surface of the other side of the hydrogen-sensitive material.

In some embodiments, a working voltage of the semiconductor resistive hydrogen sensor is greater than 0 V and not greater than 3 V.

The present disclosure also provides an intelligent hydrogen sensing system, including a sensing and transmission system and a remote monitoring system, wherein the sensing and transmission system includes a power supply unit, a hydrogen sensor unit, a data processing unit, and a data transmission unit, the hydrogen sensor unit including the semiconductor resistive hydrogen sensor as described in the above technical solutions.

The present disclosure provides use of the hydrogen-sensitive material resistant to humidity interference, the semiconductor resistive hydrogen sensor, and the intelligent hydrogen sensing system as described in the above technical solutions in selective identification of hydrogen.

The present disclosure provides a hydrogen-sensitive material resistant to humidity interference, including a 3D porous non-conductive metal oxide substrate, a nano-scale $WO_{3-x}$ film deposited on an outer surface and an inner pore surface of the 3D porous non-conductive metal oxide substrate, and Pd nanoclusters diffusely distributed on a surface of the nano-scale $WO_{3-x}$ film, wherein the nano-scale $WO_{3-x}$ film is formed from oxygen vacancy-containing tungsten oxide. In the present disclosure, the 3D porous non-conductive metal oxide substrate has a large specific surface area, which is conducive to the interaction between a produced gas-sensitive material and a gas and improves the gas-sensitive response performance. In the present disclosure, because there are oxygen vacancies in the tungsten oxide and the oxygen vacancies have an ability to decompose water at a specified temperature, the hydrogen-sensitive material thus has an ability to resist humidity interference. Under different humidities, the initial resistance of the hydrogen-sensitive material does not change with the humidity, and the response sensitivity of the hydrogen-sensitive material to hydrogen does not change with the humidity, either. In the present disclosure, the nano-scale Pd nanoclusters have a selective catalytic effect on hydrogen. Pd would preferentially catalyze the dissociation of hydrogen into hydrogen atoms to provide improved reactivity. In addition, $WO_{3-x}$ in the nano-scale $WO_{3-x}$ film and Pd nanoclusters both have a nano-scale particle size and high surface activity, which could reduce a working temperature of the gas-sensitive material. Therefore, the hydrogen-sensitive material according to the present disclosure has an ability to resist humidity interference, exhibits excellent selectivity for hydrogen, and has a low working temperature.

The present disclosure provides a method for preparing the hydrogen-sensitive material resistant to humidity interference as described in the above technical solutions. The present disclosure adopts the ALD technology to prepare the hydrogen-sensitive material. The ALD technology allows the effective and uniform deposition of a nano-film on surfaces and inside pores of 3D porous non-conductive metal oxide substrates with different thicknesses, could accurately control the thickness and uniformity of deposition, ensure the consistency of manufactured devices, and is thus conducive to the large-scale production of sensor materials.

The example results show that the initial resistance of a semiconductor resistive hydrogen sensor manufactured with the hydrogen-sensitive material according to the present disclosure substantially does not change under different humidity conditions, and a change rate could be controlled within 3%. Moreover, when different humidities are set and 100 ppm hydrogen is introduced, the resistance of the hydrogen sensor decreases first and then is substantially stable, the response sensitivity calculated accordingly (dividing the initial resistance of the gas sensor by the resistance under 100 ppm hydrogen) does not fluctuate greatly, and a fluctuation could be controlled within 10%. Compared with the initial resistance fluctuation of 50% and the response sensitivity fluctuation of 30% for the traditional gas sensors, the hydrogen sensor of the present disclosure has a significant anti-humidity interference characteristic, which is not exhibited by the general hydrogen sensors. The hydrogen sensor of the present disclosure has excellent selectivity, and the response sensitivity of the hydrogen sensor to hydrogen is tens or even hundreds of times the response sensitivity of the hydrogen sensor to other gases (such as carbon monoxide, ethanol, toluene, and formaldehyde). A working temperature of the hydrogen sensor of the present disclosure is as low as 100° C., and at this temperature, the response of the hydrogen sensor to 100 ppm hydrogen is 30.

BRIEF DESCRIPTION OF THE DRAWINGS

FIG. 1A to FIG. 1D show a schematic flow chart of preparing a hydrogen-sensitive material based on an ALD technology and transmission electron microscopy (TEM) images of a 3D porous anodic aluminum oxide (AAO) substrate, a $WO_{3-x}$ film (10 nm) produced after 100 cycles, and Pd nanoclusters (1 nm) produced after 10 cycles in Example 1, in which, FIG. 1A shows the schematic flow chart of preparing the hydrogen-sensitive material; and FIG. 1B to FIG. 1D are TEM images of the 3D porous AAO substrate, the $WO_{3-x}$ film (10 nm) produced after 100 cycles, and the Pd nanoclusters (1 nm) produced after 10 cycles, respectively.

FIG. 9A to FIG. 9B show schematic diagrams of the intelligent hydrogen sensing system in Example 3, in which, FIG. 9A shows a schematic diagram of a sensing and transmission system in the intelligent hydrogen sensing system, and FIG. 9B shows a schematic diagram of a display interface of a remote monitoring system, namely, a smartphone APP.

DETAILED DESCRIPTION OF THE EMBODIMENTS

Figure 1A:
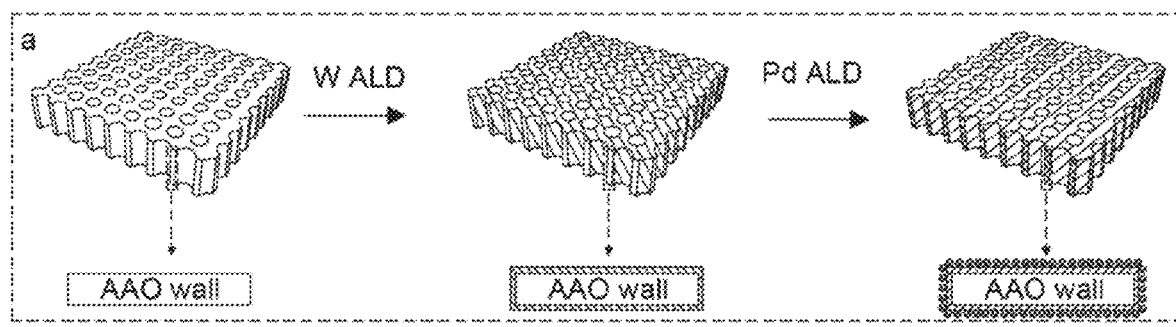

The present disclosure provides a hydrogen-sensitive material resistant to humidity interference, including a 3D non-conductive metal oxide substrate, a nano-scale $WO_{3-x}$ film deposited on an outer surface and an inner pore surface of the 3D non-conductive metal oxide substrate, and Pd nanoclusters diffusely distributed on a surface of the nano-scale $WO_{3-x}$ film, wherein the nano-scale $WO_{3-x}$ film is formed from oxygen vacancy-containing tungsten oxide.

In the present disclosure, there is no special requirements for a specific type of the 3D porous non-conductive metal oxide substrate, and a 3D porous non-conductive metal oxide substrate well known to those skilled in the art may be adopted, specifically such as a 3D porous aluminum oxide (anodic aluminum oxide, such as AAO) substrate and a 3D porous titanium oxide substrate. In some embodiments of the present disclosure, the 3D porous non-conductive metal oxide substrate has a thickness of 10 μm to 1 mm and preferably 30 μm to 50 μm, and a pore size of 50 nm to 400 nm and preferably 200 nm to 300 nm. In the present disclosure, there is no special requirements for a source of the 3D porous non-conductive metal oxide substrate, and the 3D porous non-conductive metal oxide substrate may be a commercially-available product well known to those skilled in the art or may be prepared by a method well known to those skilled in the art. In the present disclosure, the 3D porous non-conductive metal oxide substrate has a self-supporting ability and a 3D porous structure. The 3D porous non-conductive metal oxide substrate has a larger specific surface area than a substrate with a plain sheet structure, and includes channels conducive to gas diffusion, which could enhance the effective collision with gas molecules and improve the gas-sensitive response performance.

In some embodiments of the present disclosure, the nano-scale $WO_{3-x}$ film has a thickness of 5 nm to 50 nm and preferably 10 nm to 25 nm. In the present disclosure, the nano-scale $WO_{3-x}$ film is formed from oxygen vacancy-containing tungsten oxide. Oxygen vacancies existed in the tungsten oxide have an ability to decompose water at a specified temperature, resulting in an ability to resist humidity interference.

In some embodiments of the present disclosure, the Pd nanoclusters each have a particle size of 0.5 nm to 5 nm and preferably 1 nm to 3 nm. In some embodiments, a mass content of the Pd nanoclusters in the hydrogen-sensitive material ranges from 0.1% to 10% and preferably from 1% to 5%. In the present disclosure, the nano-scale Pd clusters have a selective catalytic function on hydrogen, and Pd would preferentially catalyze the dissociation of hydrogen into hydrogen atoms, thereby providing improved reactivity.

A semiconductor resistive gas sensor relies on a change in an electrical signal of a semiconductor caused by a chemical interaction between a gas molecule and a surface of a semiconductor gas-sensitive material to identify the gas molecule. However, humidity in an environment is always changing, and the changed humidity would interact with the surface of the semiconductor gas-sensitive material to cause a change of an electrical signal (initial resistance and response sensitivity). Therefore, the interference of humidity would affect the identification and detection of a target gas. In the present disclosure, nano-scale oxygen vacancy-containing $WO_{3-x}$ is deposited on the outer surface and the inner pore surface of the 3D porous non-conductive metal oxide substrate, and the hydrogen-sensitive material resistant to humidity interference is obtained by modifying metal Pd particles. The hydrogen-sensitive material exhibits excellent selectivity for hydrogen, and thus could be used in the selective identification of hydrogen.

The present disclosure provides a method for preparing the hydrogen-sensitive material resistant to humidity interference as described in the above technical solutions, including the following steps:

conducting a first ALD on a 3D porous AAO substrate by using bis(tert-butylimino)bis(dimethylamino)tungsten (VI) as a tungsten source and ozone as a precursor source, to obtain a nano-scale $WO_{3-x}$ film-deposited 3D porous substrate, wherein the first ALD is conducted at a temperature of 200° C. to 400° C., and an introduction time ratio of the tungsten source to the ozone is in a range of 1:(1-2.5); and conducting a second ALD on the nano-scale $WO_{3-x}$ film-deposited 3D porous substrate by using bis(hexafluoroacetylacetonato) palladium as a Pd source and vaporized anhydrous hydrazine as a precursor source, to obtain the hydrogen-sensitive material resistant to humidity interference, wherein the second ALD is conducted at a temperature of 180° C. to 220° C.

In the present disclosure, there are no special requirements for a device adopted for the first ALD and the second ALD, and an ALD device well to those skilled in the art may be adopted. In some embodiments of the present disclosure, the first ALD is conducted 50 to 500 times and preferably 100 to 250 times. In some embodiments, during a single time of the first ALD, an introduction time ratio of the tungsten source to the ozone is in a range of 1:(1-2.5) and preferably 1:1. In some embodiments, an introduction time of the tungsten source is 2,000 ms. In some embodiments, a residence time of the tungsten source is greater than 0 s and not less than 30 s and preferably 5 s. In some embodiments, a residence time of the ozone ranges from 5 s to 10 s and preferably 5 s. In some embodiments, a $WO_{3-x}$ film formed after a single time of the first ALD has a thickness of 0.05 nm to 0.2 nm and preferably 0.1 nm. In specific embodiments of the present disclosure, specific operations of a single time of the first ALD are as follows: opening a tungsten source valve of an ALD device for 2,000 ms, introducing the tungsten source into a cavity of the ALD device, and closing the corresponding pump and valve, such that a residence time of the tungsten source in the cavity is greater than 0 s and not less than 30 s; opening corresponding pump and valve, and cleaning for 30 s; opening a precursor source valve of the ALD device for 2,000 ms, introducing ozone into the cavity of the ALD device, and closing the corresponding pump and valve, such that a residence time of ozone ranges from 5 s to 10 s; and opening the corresponding pump and valve and cleaning for 30 s. When the first ALD is conducted multiple times, the above operation may be conducted repeatedly to deposit nano-scale $WO_{3-x}$ films with different thicknesses. In the present disclosure, the first ALD is performed at a temperature (i.e., a temperature in the cavity of the ALD device) of 200° C. to 400° C. and preferably 300° C. During the first ALD, the tungsten source is first adsorbed onto a pore wall of the 3D porous non-conductive metal oxide substrate, and organic functional group(s) of the tungsten source is removed through oxidation of the precursor source (i.e., the ozone) at a certain temperature to produce tungsten oxide. However, due to an insufficient ozone content and a relatively-low temperature (the first ALD being conducted at a temperature of 200° C. to 400° C.), oxygen vacancy-containing $WO_{3-x}$ is formed. When the temperature for the first ALD exceeds 400° C., tungsten oxide produced has no oxygen vacancies.

In some embodiments of the present disclosure, the second ALD is conducted 1 to 100 times and preferably 10 to 50 times. In some embodiments of the present disclosure, during a single time of the second ALD, a residence time of the Pd source is greater than 0 s and not less than 30 s and preferable 5 s. In some embodiments, a residence time of the vaporized anhydrous hydrazine ranges from 5 s to 10 s and preferably 5 s. In some embodiments, specific operations of a single time of the second ALD are as follows: opening a Pd source valve of an ALD device for 1,000 ms, introducing the Pd source into a cavity of the ALD device, and closing corresponding pump and valve, such that a residence time of the Pd source in the cavity is greater than 0 s and not less than 30 s; opening corresponding pump and valve, and cleaning for 30 s; opening a precursor source valve of the ALD device for 200 ms, introducing vaporized anhydrous hydrazine into the cavity of the ALD device, and closing the corresponding pump and valve, such that a residence time of the vaporized anhydrous hydrazine in the cavity ranges from 5 s to 10 s; and opening the corresponding pump and valve, and cleaning for 30 s. When the second ALD is conducted multiple times, the above operation could be conducted repeatedly to deposit Pd nanoclusters with different particle sizes. In the present disclosure, the second ALD (namely, a temperature in the cavity of the ALD device) is performed at a temperature of 180° C. to 220° C. and preferably 200° C. During the second ALD, the organic palladium source and the anhydrous hydrazine vapor react, and the anhydrous hydrazine could effectively remove organic functional group (s) of the organic palladium source to produce Pd nanoclusters. During this process, a temperature for deposition could not be too high, or Pd would be oxidized into PdO.

Compared with physical vapor deposition, the ALD technology adopted by the present disclosure could accurately control the thickness and uniformity of a gas-sensitive material, and allows the uniform deposition of a gaseous material in pores of 3D porous non-conductive metal oxide substrates with different thicknesses (10 μm to 1 mm), which could not be realized by physical vapor deposition. Compared with the traditional hydrothermal method (gas-sensitive materials prepared by the traditional hydrothermal method generally have a micro-scale particle size), a gas-sensitive material prepared by the ALD method of the present disclosure has a uniform thickness, a nano-scale particle size, and high surface activity.

The present disclosure provides a semiconductor resistive hydrogen sensor, including the hydrogen-sensitive material resistant to humidity interference as described in the above technical solutions or the hydrogen-sensitive material resistant to humidity interference prepared by the method as described in the above technical solutions, a heating electrode fixed on a surface of one side of the hydrogen-sensitive material, and a sensing electrode fixed on a surface of the other side of the hydrogen-sensitive material. In the present disclosure, a function of the heating electrode is to heat the sensor by applying a voltage to the heating electrode, and different working temperatures of the sensor could be allowed by controlling different voltages. A function of the sensing electrode is to transmit an electrical signal. In some embodiments, the sensing electrode is connected to an electrical signal meter. In the present disclosure, there are no special requirements for the heating electrode and the sensing electrode, as long as the above functions could be realized. In some embodiments of the present disclosure, the heating electrode and the sensing electrode are Pt electrodes, and the heating electrode and the sensing electrode could also be provided with different patterns, which are not particularly limited by the present disclosure. In some embodiments of the present disclosure, a manner for fixing could be specifically as follows: the hydrogen-sensitive material is sandwiched between the heating electrode and the sensing electrode. In some embodiments of the present disclosure, a working voltage of the semiconductor resistive hydrogen sensor is greater than 0 V and not less than 3 V and preferably 1.2 V (a working temperature corresponding to 1.2 V is 100° C.). The semiconductor resistive hydrogen sensor according to the present disclosure has an ability to resist humidity interference, exhibits excellent selectivity for hydrogen, and has a low working temperature, and a lower detection limit of 100 ppb.

The present disclosure provides use of the semiconductor resistive hydrogen sensor in selective identification of hydrogen. In some embodiments of the present disclosure, a method of the use is as follows: heating the sensor by applying a voltage between two ends of the heating electrode; bringing gas molecules to interact with the $Pd/WO_{3-x}$ gas-sensitive material deposited in the sensor at a certain working temperature, thereby changing the resistance of the gas-sensitive material; and determining a concentration value of a gas through a change value of an electrical signal reflected by the sensing electrode. In some embodiments, the concentration information of hydrogen could be obtained according to concentration-electrical signal change value standard curve calibrated and established early.

The present disclosure also provides an intelligent hydrogen sensing system, including a sensing and transmission system and a remote monitoring system, wherein the sensing and transmission system includes a power supply unit, a hydrogen sensor unit, a data processing unit, and a data transmission unit, the hydrogen sensor unit including the semiconductor resistive hydrogen sensor as described in the above technical solutions. In the present disclosure, the power supply unit is configured to provide energy for an operation of the system. In some embodiments, the data processing unit is a microcontroller unit (MCU), and is configured to read and process data of the system. In some embodiments, the data transmission unit is composed of Bluetooth units, and is configured to pack data and send packed data wirelessly. In some embodiments, the data transmission unit is a smartphone APP matching with the sensing and transmission system, and is configured to allow the remote view of concentration information of various gases at each point. In the present disclosure, there are no special requirements for a connection relationship among the sensing and transmission system, the power supply unit, the hydrogen sensor unit, the data processing unit, and the data transmission unit, as long as the smooth transmission of a signal could be guaranteed.

The present disclosure provides use of the intelligent hydrogen sensing system in selective identification of hydrogen. In some embodiments of the present disclosure, a method of the use is as follows: subjecting an electrical signal generated by the hydrogen sensor unit to analog-to-digital conversion and noise-reducing filtering in the data processing unit, then inputting a resulting data into the data transmission unit; packing the data in the data transmission unit, and wirelessly transmitting and uploading the packed data to a matching remote monitoring system; and converting an electrical signal to a concentration value through a built-in concentration-electrical signal change value standard curve in the remote monitoring system, such that the gas concentration information at each detection point could be viewed remotely through the remote monitoring system and a hydrogen concentration value could be obtained selectively.

The hydrogen-sensitive material resistant to humidity interference, the semiconductor resistive hydrogen sensor, and the intelligent hydrogen sensing system and the preparation and use thereof according to the present disclosure are described in detail below in conjunction with examples, but these examples should not be understood as a limitation to the scope of the present disclosure.

Example 1

A hydrogen-sensitive material resistant to humidity interference was provided, and prepared according to the following procedures:

1) Deposition of a nano-scale $WO_{3-x}$ film: A single cycle was as follows: A 3D porous AAO substrate (with a pore size of 400 nm and a thickness of 50 μm) was placed in an ALD cavity. Bis(tert-butylimino)bis(dimethylamino)tungsten (VI) was used as a tungsten source. A tungsten source valve of ALD was opened for 2,000 ms, the corresponding pump and valve were closed, and a residence time of the tungsten source in the cavity (a temperature in the cavity was 300° C.) was 5 s. The corresponding pump and valve were opened to clean the unreacted tungsten source for 30 s. An ozone valve of ALD was opened for 2,000 ms, the corresponding pump and valve were closed, and a residence time of ozone in the cavity was 5 s. The corresponding pump and valve were opened to clean the unreacted ozone for 30 s. A $WO_{3-x}$ film deposited after the above single cycle had a thickness of about 0.1 nm. 100 cycles were conducted in total to deposit a 10 nm-thick nano-scale $WO_{3-x}$ film (oxygen vacancy-containing tungsten oxide) on an outer surface and an inner pore surface of the 3D porous AAO substrate.

2) Deposition of Pd nanoclusters on a nano-scale $WO_{3-x}$ film-deposited 3D porous AAO substrate obtained in the step 1): A single cycle was as follows: Bis(hexafluoroacetylacetonato) palladium was used as a palladium (Pd) source. A Pd source valve of ALD was opened for 1,000 ms, the corresponding pump and valve were closed, and a residence time of the Pd source in the cavity (a temperature in the cavity was 200° C.) was 5 s. The corresponding pump and valve were opened to clean the unreacted Pd source for 30 s. An anhydrous hydrazine valve of ALD was opened for 200 ms, the corresponding pump and valve were closed, and a residence time of vaporized anhydrous hydrazine in the cavity was 5 s. The corresponding pump and valve were opened to clean the unreacted anhydrous hydrazine for 30 s. 10 cycles were conducted in total to deposit Pd nanoclusters with a particle size of 1 nm on the nano-scale $WO_{3-x}$ film-deposited 3D porous AAO substrate, so as to obtain the hydrogen-sensitive material resistant to humidity interference.

Figure 1B:
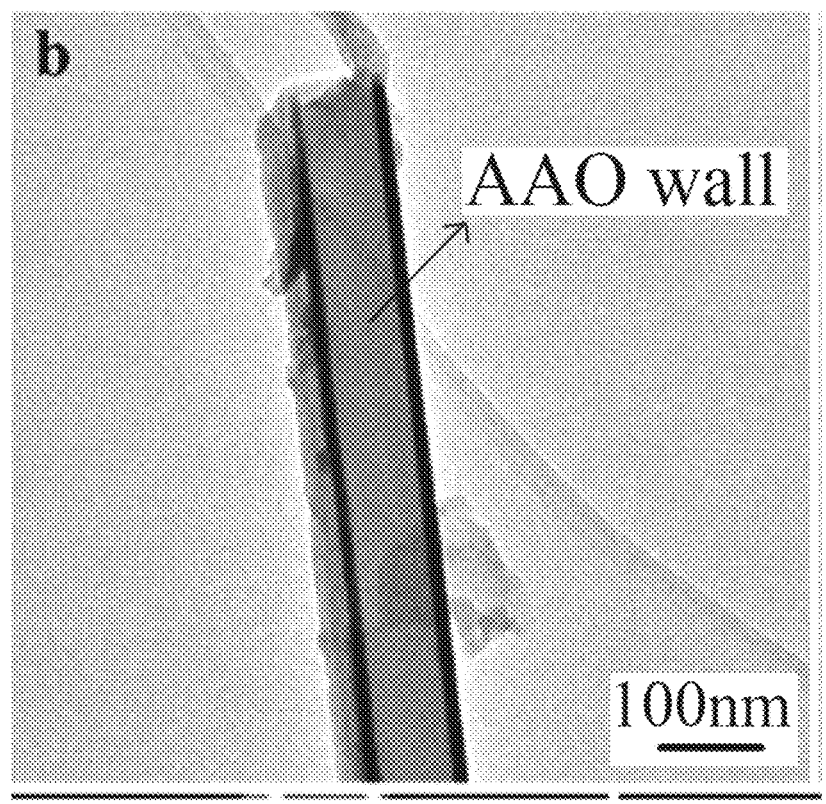
Figure 1C:
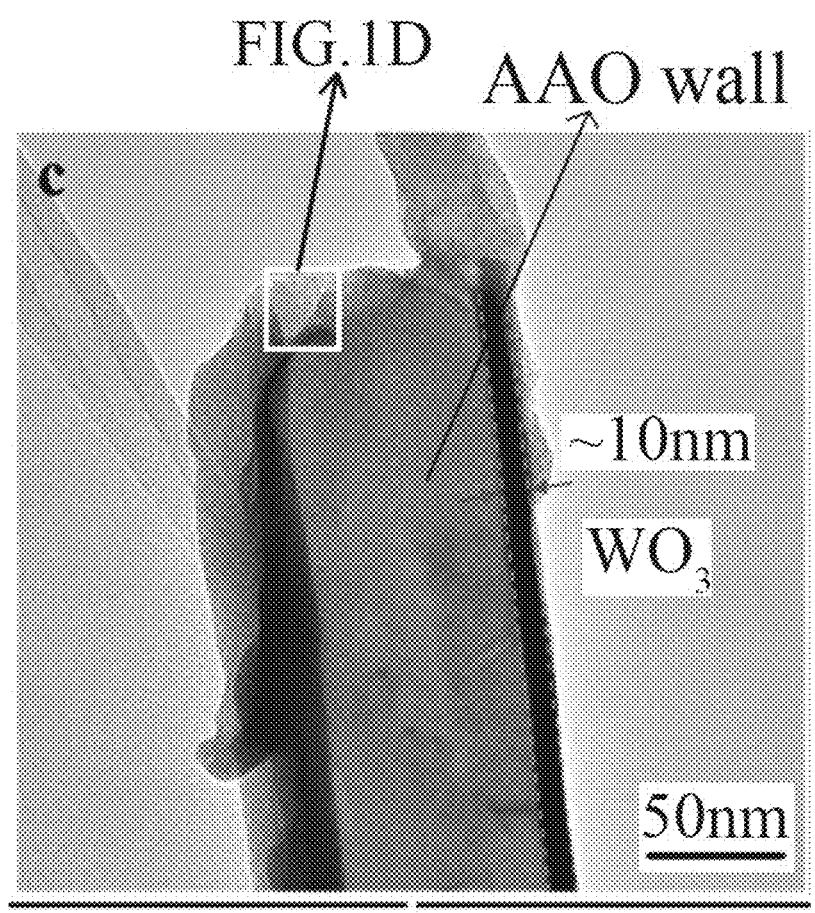
Figure 1D:
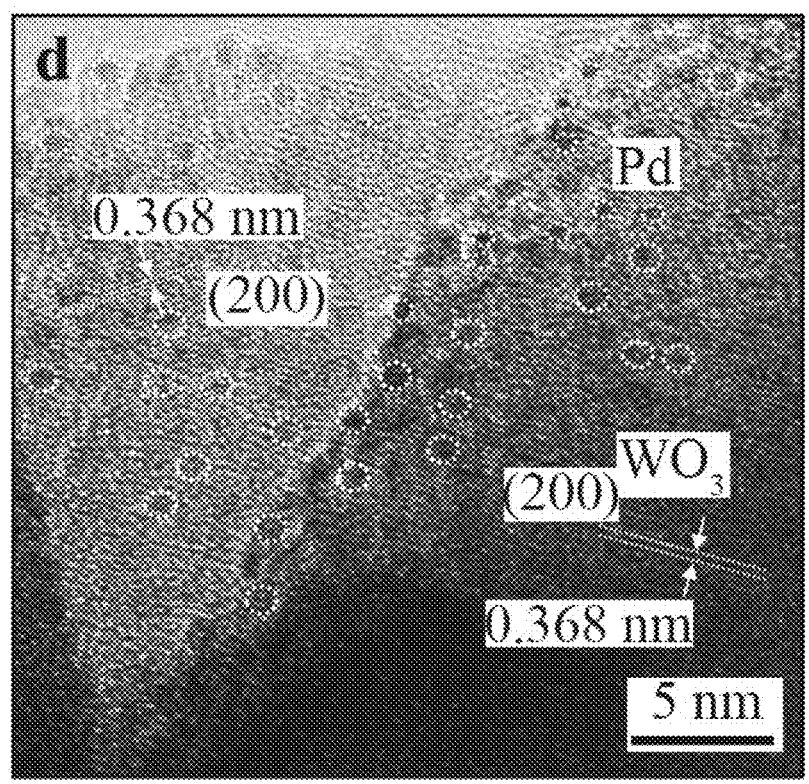

FIG. 1A to FIG. 1D show a schematic flow chart of preparing the hydrogen-sensitive material based on the ALD technology and TEM images of the 3D porous AAO substrate, the $WO_{3-x}$ film (10 nm) produced after 100 cycles, and the Pd nanoclusters (1 nm) produced after 10 cycles in Example 1. FIG. 1A shows the schematic flow chart of preparing the hydrogen-sensitive material based on the ALD technology; and FIG. 1B to FIG. 1D are TEM images of the 3D porous AAO substrate, the $WO_{3-x}$ film (10 nm) produced after 100 cycles, and the Pd nanoclusters (1 nm) produced after 10 cycles, respectively. As can be seen from FIG. 1A to FIG. 1D, a thickness of the $WO_{3-x}$ film deposited on the surface of the AAO is 10 nm, the Pd nanoclusters deposited subsequently are diffusely distributed and have a particle size of 1 nm, and a lattice spacing of the lattice plane (200) of the Pd nanoclusters is 0.368 nm.

Example 2

Figure 2:
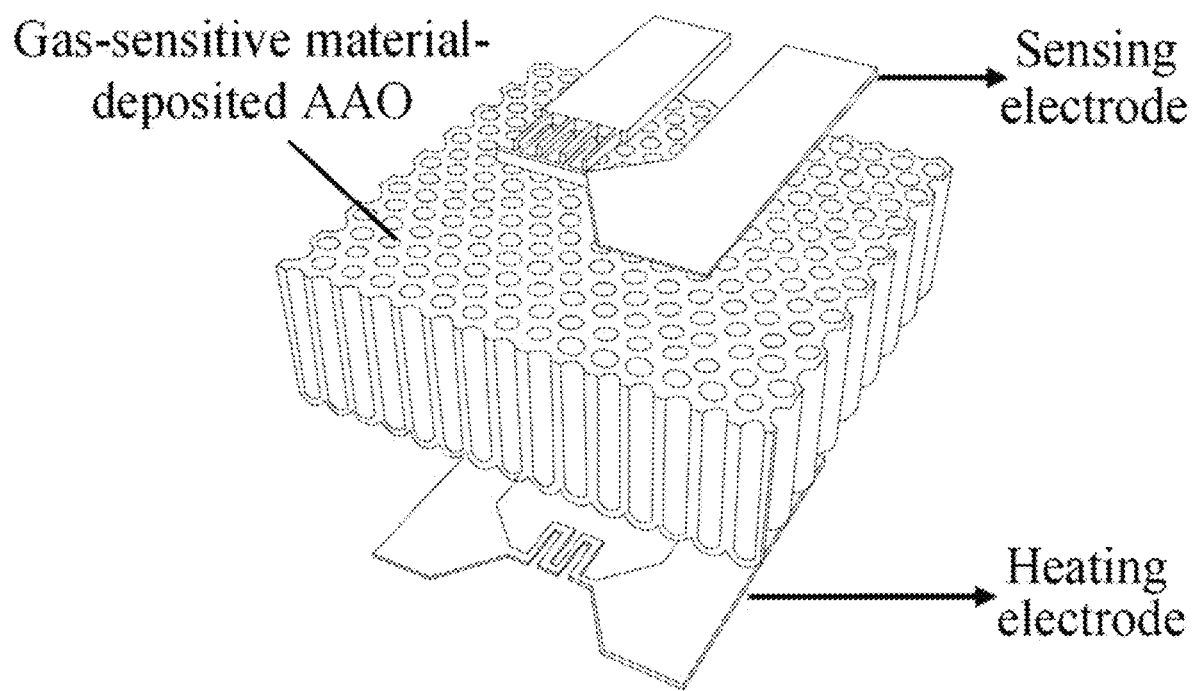
FIG. 2 shows a schematic structural diagram of the semiconductor resistive hydrogen sensor in Example 2.

A semiconductor resistive hydrogen sensor was prepared as follows:

Upper and lower electrode templates shown in FIG. 2 were designed, and Pd/$WO_{3-x}$-deposited AAO (i.e., the hydrogen-sensitive material) obtained in Example 1 was sandwiched between the two electrode templates. A 100 nm Pt electrode was deposited on each of front and back sides of the AAO through magnetron sputtering, wherein the upper one was a sensing electrode for the transmission of an electrical signal and the lower one was a heating electrode for the heating of the sensor.

Figure 4:
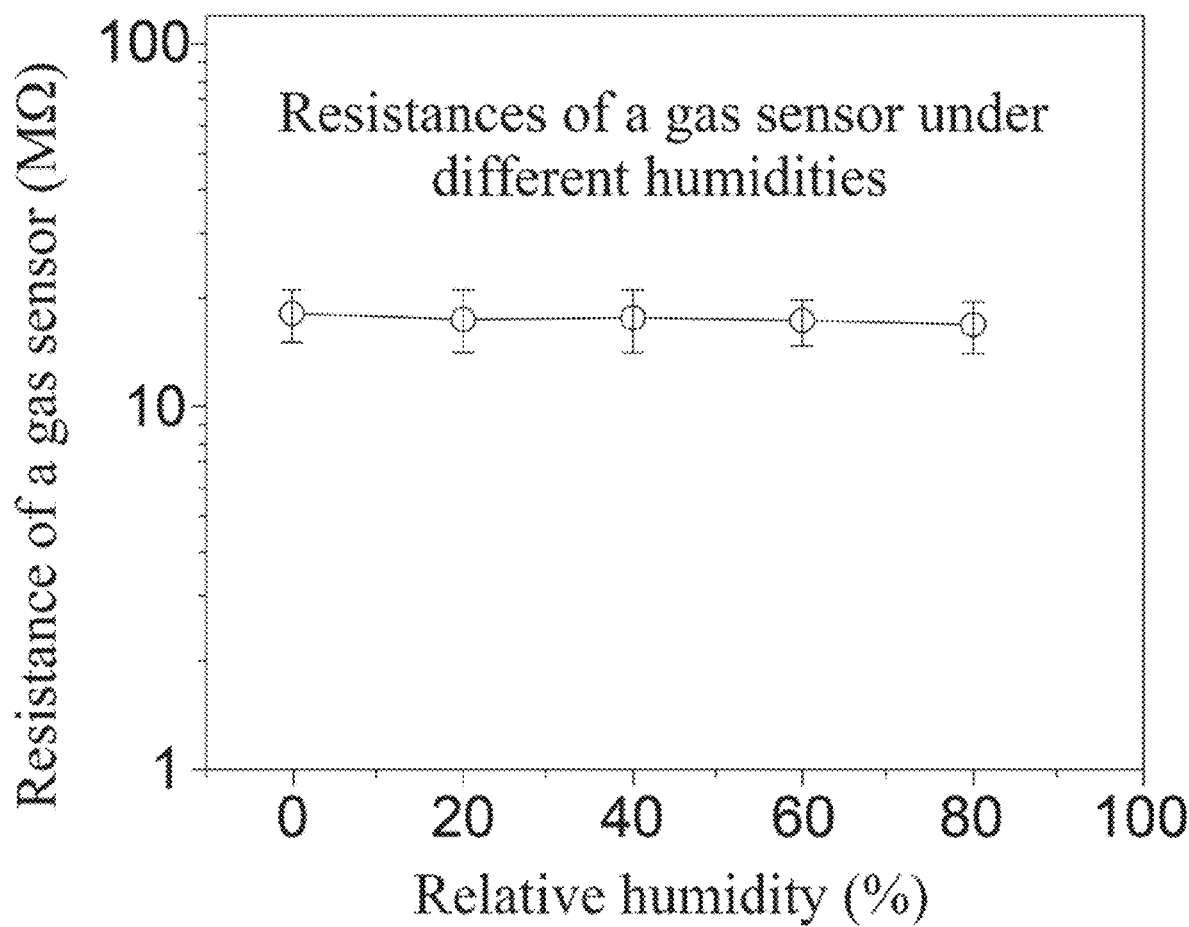
FIG. 4 shows the initial resistances of the hydrogen sensor in Example 2 at different humidities.
Figure 5:
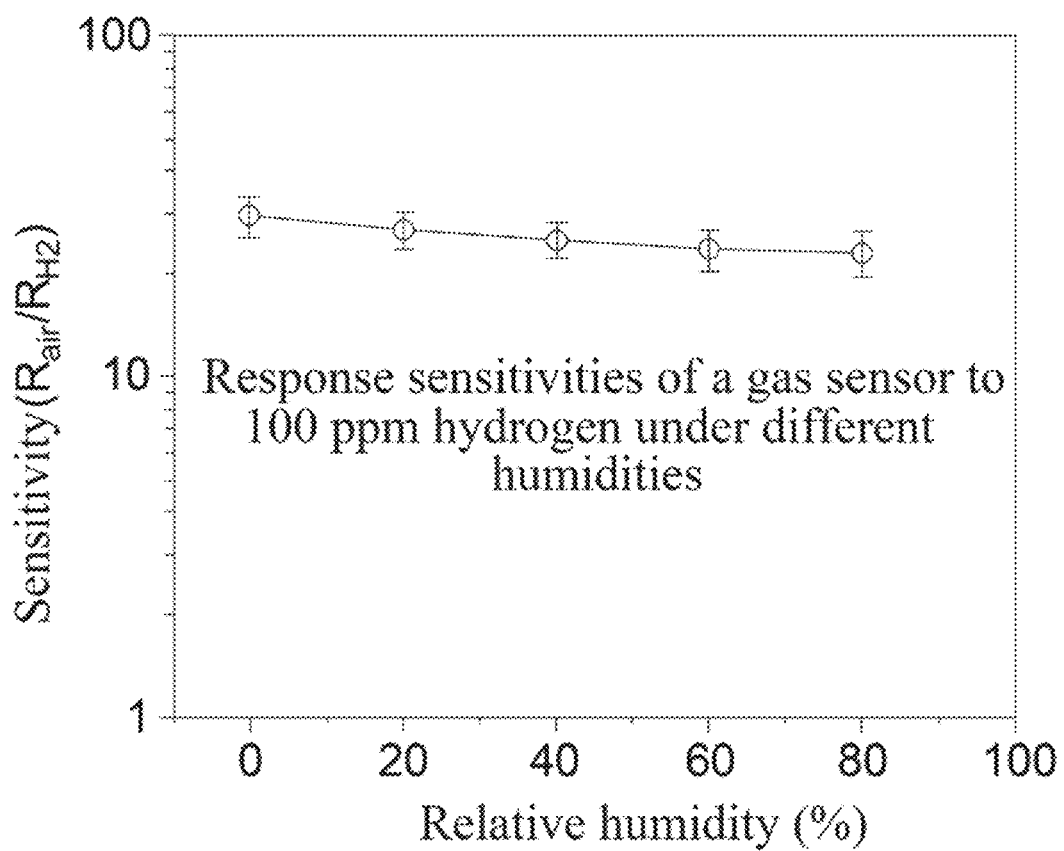
FIG. 5 shows the response sensitivities of the hydrogen sensor in Example 2 to 100 ppm hydrogen at different humidities.

The semiconductor resistive hydrogen sensor was subjected to performance tests as follows:

(a) Humidity resistance test by a test method as follows: A mixing ratio of 100% humidity air to dry air was controlled by a test system to control a humidity of a test environment at 0% to 100%. The anti-humidity interference ability of the gas sensor was determined according to a change in an electrical signal of the gas sensor: 1) The anti-humidity interference ability was determined by testing baseline resistance (i.e., the initial resistance ($R_{air}$) of the sensor) under different humidities and comparing changes thereof. Baseline resistance values $R_{air}$ were extracted from FIG. 3 and used for plotting, and results are shown in FIG. 4. 2) The anti-humidity interference ability was determined by testing response values of the gas sensor to 100 ppm hydrogen under different humidities. Response values were extracted from FIG. 3 and used for plotting, and results are shown in FIG. 5.

Figure 3:
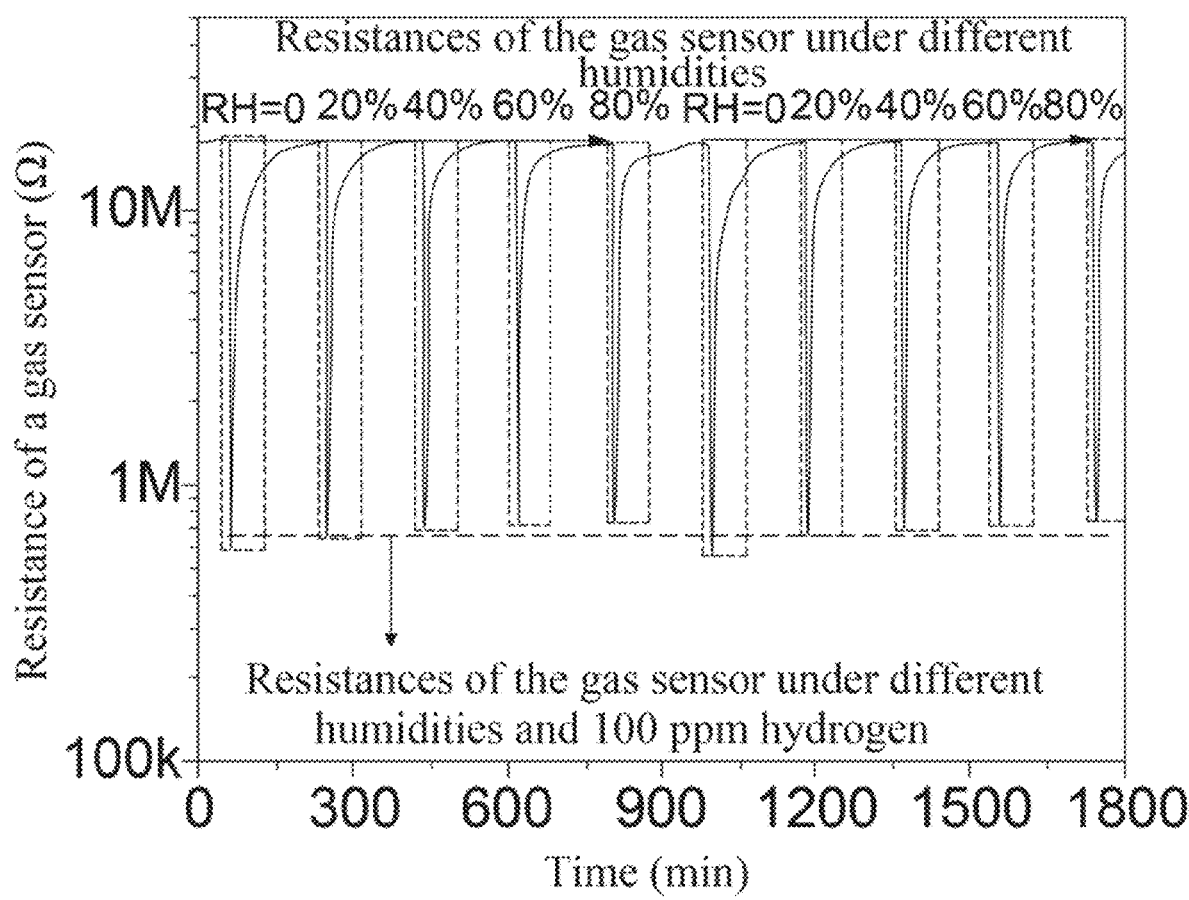
FIG. 3 shows a resistance signal change diagram when the hydrogen sensor in Example 2 is in response to 100 ppm hydrogen at different humidities (RH=0%, 20%, 40%, 60%, and 80%).

FIG. 3 shows a resistance signal change diagram when the hydrogen sensor is in response to 100 ppm hydrogen at different humidities (RH=0%, 20%, 40%, 60%, and 80%). FIG. 4 shows the initial resistances of the sensor at different humidities. FIG. 5 shows the response sensitivities of the hydrogen sensor to 100 ppm hydrogen at different humidities. As can be seen from FIG. 3 to FIG. 5, the initial resistance of the hydrogen sensor (at a working temperature of 80° C.) substantially does not change under different humidity conditions, and a change rate could be controlled within 3%. Moreover, when different humidities are set and 100 ppm hydrogen is introduced, the resistance of the sensor decreases first and then is substantially stable, the response sensitivity calculated accordingly (dividing the initial resistance ($R_{air}$) of the sensor by the resistance ($R_{H2}$) under 100 ppm hydrogen) does not fluctuate greatly, and a fluctuation could be controlled within 10%. Compared with the initial resistance fluctuation of 50% and the response sensitivity fluctuation of 30% for the traditional gas sensors, the hydrogen sensor prepared in the present disclosure has a significant anti-humidity interference characteristic.

(b) Selectivity test by a test method as follows: Response sensitivities of the hydrogen sensor prepared in Example 2 (which was denoted as a Pd/$WO_{3-x}$ gas sensor) to 10 ppm hydrogen, 10 ppm carbon monoxide, 10 ppm ethanol, 10 ppm toluene, and 10 ppm formaldehyde were separately tested, with a sensor formed from a gas-sensitive material prepared by merely depositing a nano-scale $WO_{3-x}$ film on a 3D porous AAO substrate (which was denoted as a $WO_{3-x}$ gas sensor) as a comparison.

Figure 6:
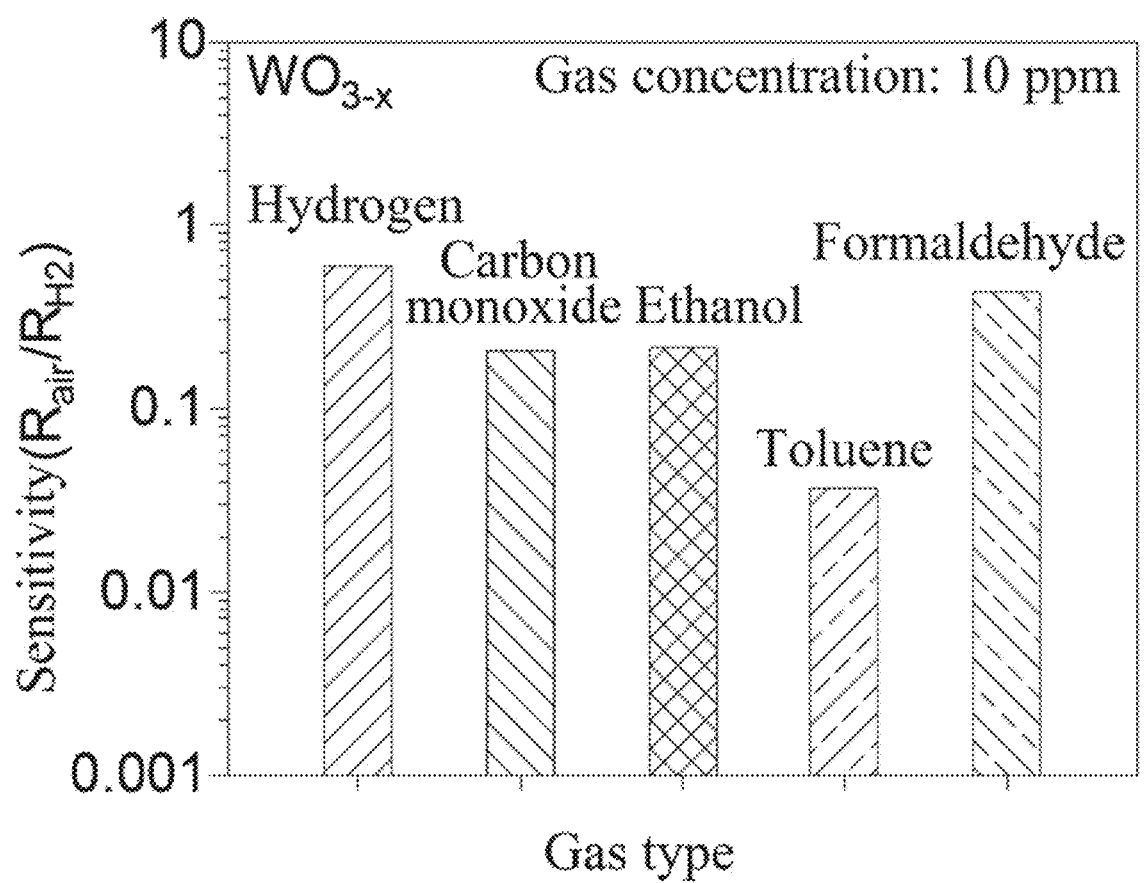
FIG. 6 shows a histogram of response sensitivities of the $WO_{3-x}$ gas sensor in Example 2 to different gases (hydrogen, carbon monoxide, ethanol, toluene, and formaldehyde).
Figure 7:
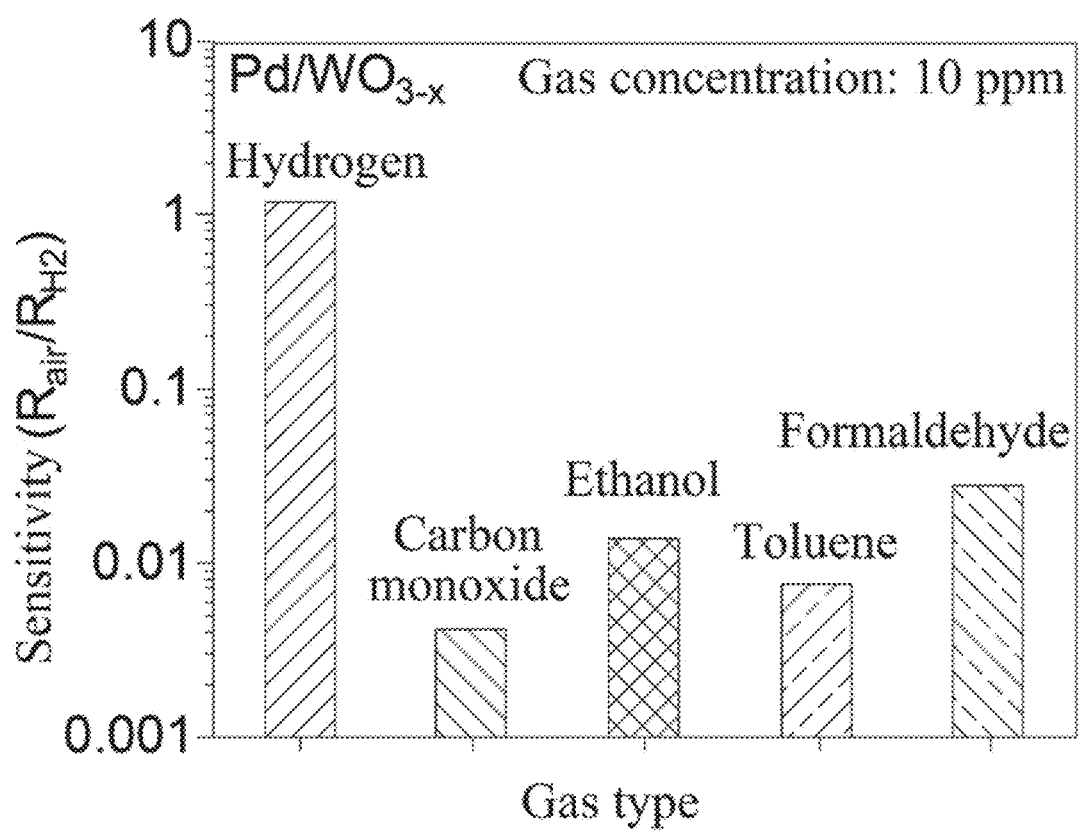
FIG. 7 shows a histogram of response sensitivities of the Pd/$WO_{3-x}$ gas sensor in Example 2 to different gases (hydrogen, carbon monoxide, ethanol, toluene, and formaldehyde).

FIG. 6 shows a histogram of response sensitivities of the $WO_{3-x}$ gas sensor to different gases (hydrogen, carbon monoxide, ethanol, toluene, and formaldehyde). FIG. 7 shows a histogram of response sensitivities of the Pd/$WO_{3-x}$ gas sensor to different gases (hydrogen, carbon monoxide, ethanol, toluene, and formaldehyde). The Pd/$WO_{3-x}$ gas sensor exhibits higher response sensitivity to hydrogen, compared with the $WO_{3-x}$ and Pd/$WO_{3-x}$ gas sensors.

Figure 8:
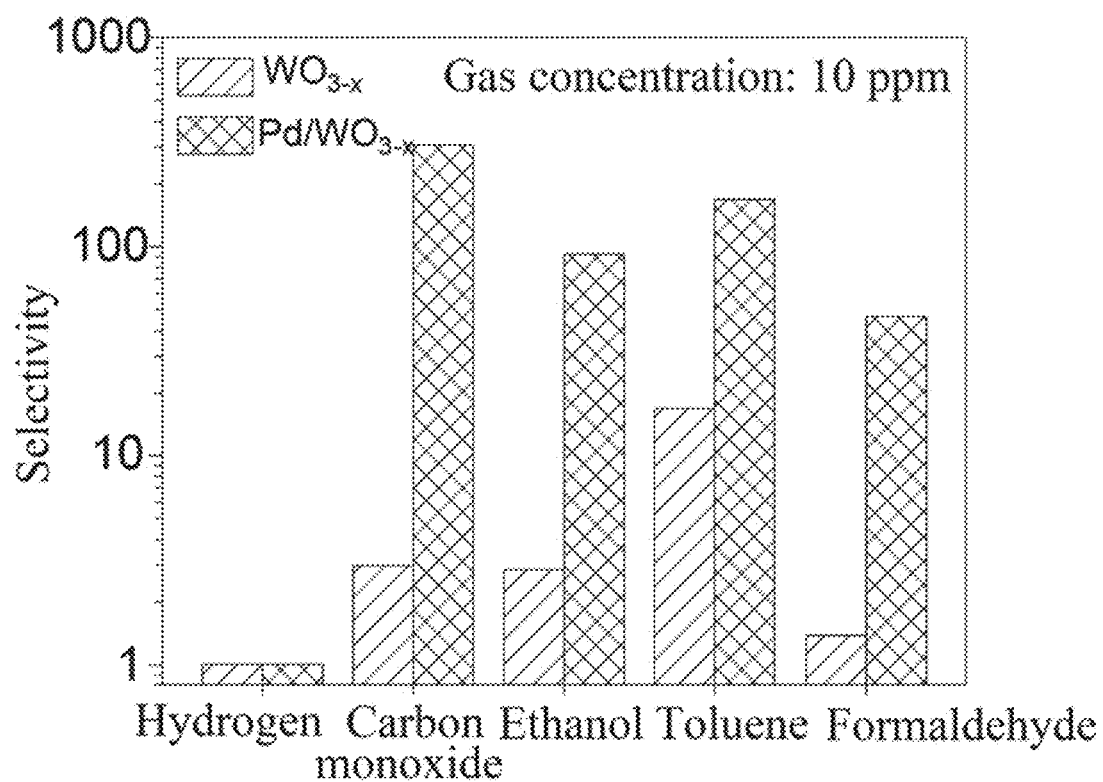
FIG. 8 shows a histogram of selectivities of the $WO_{3-x}$ gas sensor and the Pd/$WO_{3-x}$ gas sensor in Example 2 for gases.

FIG. 8 shows a histogram of selectivities of the $WO_{3-x}$ gas sensor and the Pd/$WO_{3-x}$ gas sensor for gases. The selectivity is represented by a ratio of a response sensitivity of a gas sensor to hydrogen to a response sensitivity of the gas sensor to another gas (carbon monoxide, ethanol, toluene, and formaldehyde). A higher ratio represents a better selectivity. It can be seen from FIG. 8 that the Pd/WO$_{3-x}$ gas sensor has excellent selectivity for hydrogen.

Example 3

An intelligent hydrogen sensing system is provided, being composed of a sensing and transmission system and a remote monitoring system. The sensing and transmission system is composed of a power supply unit (which is configured to provide energy for an operation of the system), a gas sensor unit, an MCU (which is configured to read and process data of the system), and a data transmission unit (which is composed of Bluetooth units, and is configured to transmit data wirelessly). The remote monitoring system is a matching smartphone APP (real-time remote monitoring).

The gas sensor unit is the semiconductor resistive hydrogen sensor prepared in Example 3. A signal generated by the gas sensor unit is subjected to analog-to-digital conversion and noise-reducing filtering in the MCU, and a resulting data is then input into the data transmission unit. The data transmission unit packs data and wirelessly sends packed data. Data of the gas sensor is uploaded to the matching smartphone APP through a Bluetooth gateway, and information of various gas concentrations at each point is remotely viewed through the smartphone APP.

Figure 9A:
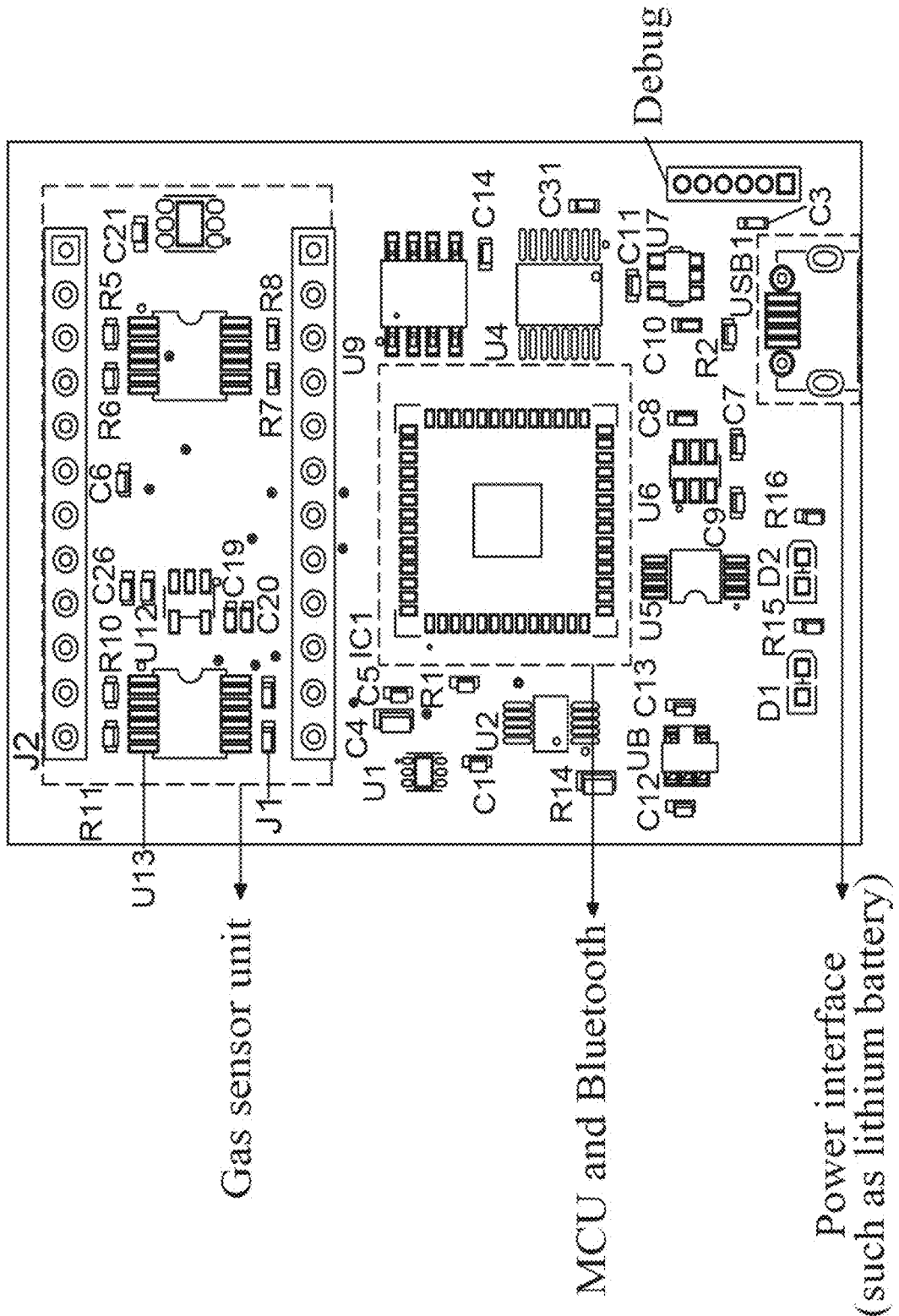
Figure 9B:
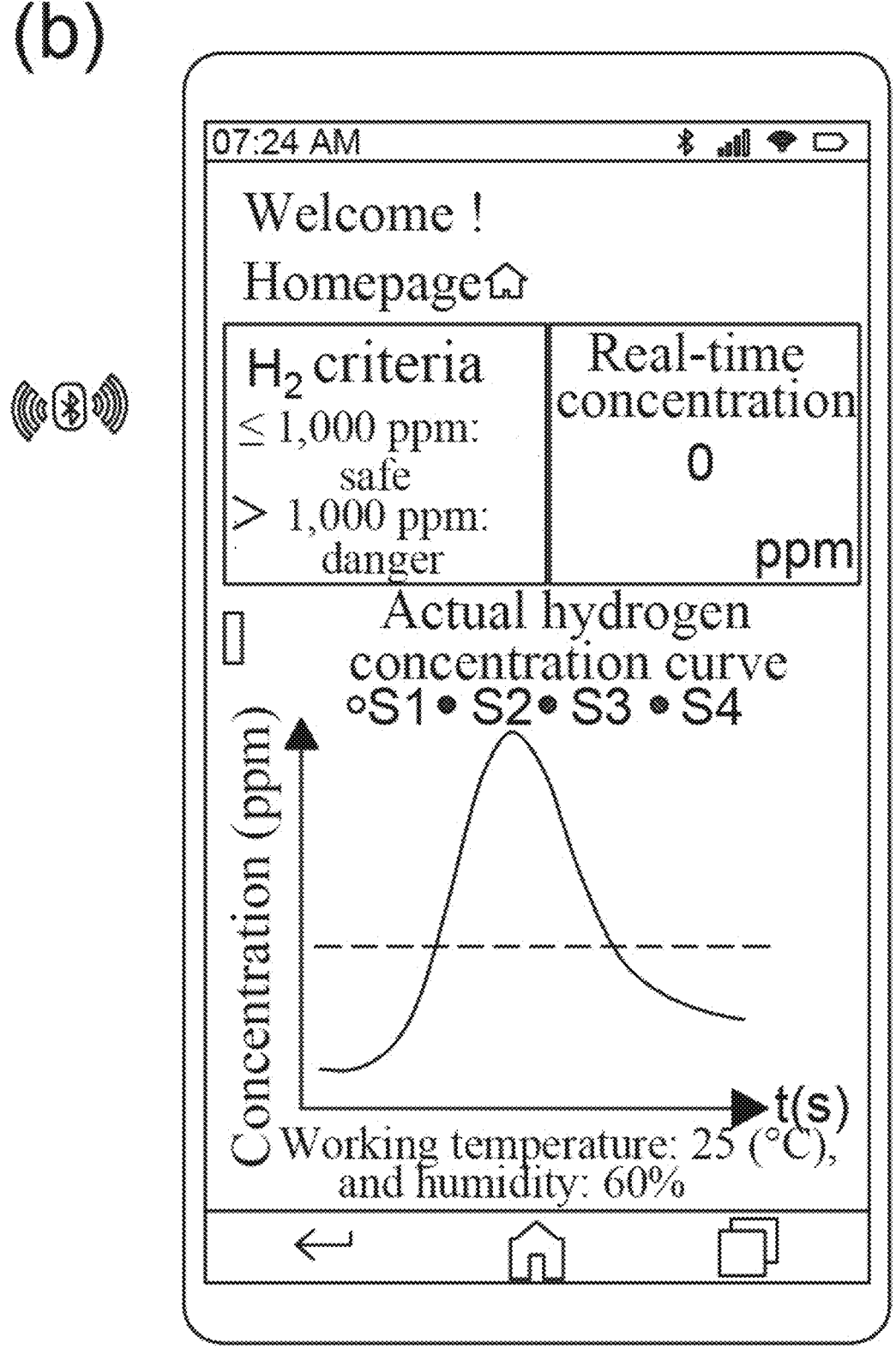

FIG. 9A to FIG. 9B show schematic diagrams of the intelligent hydrogen sensing system. FIG. 9A shows a schematic diagram of a sensing and transmission system in the intelligent hydrogen sensing system, and FIG. 9B shows a schematic diagram of a display interface of a remote monitoring system, namely, a smartphone APP.

It can be seen from the above examples that a sensor prepared from the hydrogen-sensitive material according to the present disclosure has an ability to resist humidity interference and exhibits excellent selectivity for hydrogen.

The above are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A hydrogen-sensitive material resistant to humidity interference, comprising
a three-dimensional (3D) porous non-conductive metal oxide substrate,
a nano-scale WO3-x film deposited on an outer surface and an inner pore surface of the 3D porous non-conductive metal oxide substrate, and
Pd nanoclusters diffusely distributed on a surface of the nano-scale WO3-x film,
wherein the nano-scale WO3-x film is formed from oxygen vacancy-containing tungsten oxide.

2. The hydrogen-sensitive material resistant to humidity interference as claimed in claim 1, wherein the 3D porous non-conductive metal oxide substrate has a thickness of 10 μm to 1 mm and a pore size of 50 nm to 400 nm.

3. The hydrogen-sensitive material resistant to humidity interference as claimed in claim 1, wherein the nano-scale WO3-x film has a thickness of 5 nm to 50 nm; and the Pd nanoclusters each have a particle size of 0.5 nm to 5 nm, and a mass content of the Pd nanoclusters in the hydrogen-sensitive material ranges from 0.1% to 10%.

4. A method for preparing the hydrogen-sensitive material resistant to humidity interference as claimed in claim 1, comprising the steps of
conducting a first atomic layer deposition (ALD) on the 3D porous non-conductive metal oxide substrate by using bis(tert-butylimino)bis(dimethylamino)tungsten (VI) as a tungsten source and ozone as a precursor source, to obtain a nano-scale WO3-x film-deposited 3D porous substrate, wherein the first ALD is conducted at a temperature of 200° C. to 400° C., and an introduction time ratio of the tungsten source to the ozone is in a range of 1:1 to 1:2.5; and
conducting a second ALD on the nano-scale WO3-x film-deposited 3D porous substrate by using bis(hexafluoroacetylacetonato)palladium as a Pd source and vaporized anhydrous hydrazine as a precursor source, to obtain the hydrogen-sensitive material resistant to humidity interference, wherein the second ALD is conducted at a temperature of 180° C. to 220° C.

5. The method as claimed in claim 4, wherein the first ALD is conducted 50 to 500 times, and a WO3-x film formed after a single time of the first ALD has a thickness of 0.05 nm to 0.2 nm.

6. The method as claimed in claim 4, wherein the second ALD is conducted 1 to 100 times.

7. A semiconductor resistive hydrogen sensor, comprising
the hydrogen-sensitive material resistant to humidity interference as claimed in claim 1,
a heating electrode fixed on a surface of one side of the hydrogen-sensitive material, and
a sensing electrode fixed on a surface of the other side of the hydrogen-sensitive material.

8. The semiconductor resistive hydrogen sensor as claimed in claim 7, wherein a working voltage of the semiconductor resistive hydrogen sensor is greater than 0 V and not greater than 3 V.

9. An intelligent hydrogen sensing system, comprising
a sensing and transmission system, and
a remote monitoring system,
wherein the sensing and transmission system comprises a power supply unit, a hydrogen sensor unit, a data processing unit, and a data transmission unit, the hydrogen sensor unit comprising the semiconductor resistive hydrogen sensor as claimed in claim 7.

10. A method for selective identification of hydrogen comprising:
heating the semiconductor resistive hydrogen sensor as claimed in claim 7 by applying a voltage between two ends of the heating electrode;
bringing hydrogen gas molecules to interact with the hydrogen-sensitive material in the semiconductor resistive hydrogen sensor at a working temperature, thereby changing the resistance of the hydrogen-sensitive material; and
determining a concentration value of hydrogen gas through a change value of an electrical signal reflected by the sensing electrode.

11. The intelligent hydrogen sensing system as claimed in claim 9, wherein a working voltage of the semiconductor resistive hydrogen sensor is greater than 0V and not greater than 3V.

12. A method for selective identification of hydrogen by using the intelligent hydrogen sensing system as claimed in claim 9, comprising:

subjecting an electrical signal generated by the hydrogen sensor unit to analog-to-digital conversion and noise-reducing filtering in the data processing unit, then inputting a resulting data into the data transmission unit;

packing the resulting data in the data transmission unit, and wirelessly transmitting and uploading packed data to the remote monitoring system; and converting the electrical signal to a hydrogen concentration value through a built-in concentration-electrical signal change value standard curve in the remote monitoring system, thereby obtaining the hydrogen concentration value.

\* \* \* \* \*